United States Patent [19]

Estis

[11] Patent Number: 5,110,912

[45] Date of Patent: May 5, 1992

[54] PURIFICATION OF IL-2-CONTAINING HYBRID COMPOUNDS

[75] Inventor: Leonard F. Estis, Upton, Mass.

[73] Assignee: Seragen, Inc., Hopkinton, Mass.

[21] Appl. No.: 487,604

[22] Filed: Mar. 2, 1990

[51] Int. Cl.⁵ .............................................. C07K 3/20
[52] U.S. Cl. .................................... 530/413; 530/351; 530/412; 530/417; 530/402; 530/422; 424/85.2
[58] Field of Search .............. 530/412, 422, 413, 417, 530/351

[56] References Cited

U.S. PATENT DOCUMENTS

| | | | |
|---|---|---|---|
| 4,545,985 | 10/1985 | Pastan et al. | 424/88 |
| 4,675,382 | 6/1987 | Murphy | 530/324 |
| 4,771,128 | 9/1989 | Ferris et al. | 530/412 |
| 4,892,827 | 1/1990 | Pastan et al. | 435/69.52 |

FOREIGN PATENT DOCUMENTS 0195680  9/1986  European Pat. Off. .

OTHER PUBLICATIONS

Lorberbourn-Galski et al. *PNAS* 85, 1984, pp. 1922-1926.
Kelley, *PNAS* 1988, vol. 85, pp. 3980-3984.
Bailon et al, *Biotechnolog*, Nov. 1988, pp. 1326-1329.
Perendesis et al *PNAS* 85, 1988, pp. 8386-8390.
Chaudhary et al *Nature* 339, 1989, pp. 394-397.
Kirkman et al, Transplantation 47, 1989, pp. 327-330.
Williams et al, *Protein Engineering* vol. 1(6) 1987, pp. 493-498.
Lorberbourn-Galski et al, *IBC* 263(35) 1988, pp. 18650-18656.

*Primary Examiner*—Garnette D. Draper
*Attorney, Agent, or Firm*—Fish & Richardson

[57] ABSTRACT

A method for purifying from a mixture of hybrid compound which contains a portion of IL-2, which portion includes at least a region of the IL-2R binding domain of IL-2, which region is effective to cause the hybrid compound to bind to cells containing an IL-2R. The method includes passing the mixture containing the hybrid compound over a column having attached thereto molecules consisting of or containing a complex sugar moiety with affinity for the hybrid compound, and eluting the hybrid compound with a suitable eluant. The invention also features related complexes of the hybrid compound and assays for the hybrid compound.

9 Claims, 4 Drawing Sheets

PURIFICATION OF IL-2-CONTAINING HYBRID COMPOUNDS

BACKGROUND OF THE INVENTION

This invention relates to hybrid compounds which contain a portion of Interleukin 2 (IL -2) including a region of the IL -2 receptor (IL-2R) binding domain.

Certain hybrid compounds falling within the foregoing classification are known to be of diagnostic and therapeutic value. In particular, a class of hybrid proteins of significant therapeutic value (e.g., for prevention of allograft rejection) contains the following protein segments joined together by peptide bonds: (a) the enzymatically active Fragment A of diphtheria toxin, (b) a segment including the cleavage domain adjacent Fragment A, (c) a segment including at least a portion of the hydrophobic domain of Fragment B of diphtheria toxin and not including the generalized eukaryotic binding domain of Fragment B, and (d) a segment including a portion of IL-2 which includes a region of the IL-2R binding domain of IL-2 effective to cause the hybrid protein to bind selectively to and kill a predetermined class of cells which bear an IL-2R. This class of proteins is referred to herein as DAB IL-2. (Murphy U.S. Pat. No. 4,675,382, hereby incorporated by reference.) It is important to be able to obtain highly purified preparations of IL-2-containing hybrid molecules such as DAB-IL-2 molecules in order to avoid any possible harmful effects associated with impurities in such preparations.

It is known that IL-2 can be easily purified on hydrophobic reverse phase columns. However, DAB IL-2 binds irreversibly to such resins, which therefore cannot be used to purify these hybrid proteins. There are other major differences which have been demonstrated between the binding properties of IL-2 and DAB IL-2. For instance, DAB-IL-2 typically binds with 5 10 fold lower affinity to the high affinity IL-2 receptor, as compared to IL-2 In addition, DAB-IL-2 molecules form complex intermolecular covalent (disulfide) and non covalent bonds among themselves and with the major DAB IL-2 subfragments (59 kD, 49 kD, and 47 kD) produced in *E. coli* lysates, resulting in heterogeneous oligomeric structures, e.g., 68–68 dimers, 68–49 dimers, 68–47 dimers, and 68-49-47 trimers, among others.

A recent publication by Sherblom et al., J. Immunol. 143:939–944 (1989) demonstrated that recombinant IL-2 acts as a lectin that binds specifically to a complex high mannose carbohydrate sequence found on several glycoproteins, including hen egg-white ovalbumin and human uromodulin. This high mannose sequence (referred to as M5[6], and illustrated diagrammatically in FIG. 4) has a branched bi arternary mannose component attached to a core of diacetylchitobiose. Sherblom et al., using amino acid homoloqy comparison to known lectin binding regions, hypothesized that the carbohydrate binding site of IL-2 is near its amino terminal end; it is the amino terminal end of IL-2 that is fused to the diphtheria toxin derived sequences in DAB-IL-2.

SUMMARY OF THE INVENTION

The present invention features a method for purifying, from a mixture, a hybrid compound which contains a portion of IL-2 which includes at least a region of the IL-2R binding domain of IL-2 effective to cause the hybrid compound to bind to cells containing an IL-2R. The method includes passing the mixture containing the hybrid compound over a column having attached thereto molecules consisting of or containing a complex sugar moiety with affinity for the IL-2 derived portion of the hybrid compound to bind the hybrid molecule to the sugar while permitting the remainder of the mixture to pass through the column; and then eluting the hybrid compound with a suitable eluant. In a particular embodiment, the method is used to purify from a mixture a hybrid protein composed of the protein segments (a) the enzymatically active Fragment A of diphtheria toxin, (b) a segment including the cleavage domain adjacent Fragment A, (c) at least a portion of the hydrophobic domain of Fragment B of diphtheria toxin and not including the generalized eukaryotic binding domain of Fragment B, and (d) a portion of IL-2 including a region of the IL-2R binding domain of IL-2 effective to cause the hybrid protein to selectively bind to and kill cells which contain an IL-2R.

In particular embodiments, the molecules attached to the column consist of ovalbumin, uromodulin, the sugar portion of ovalbumin, a region of the sugar portion of ovalbumin with affinity for the hybrid molecule, the sugar portion of uromodulin, or a region of the sugar portion of uromodulin with affinity for the hybrid molecule. The eluant can be one which contains a sugar which competes with the IL-2 binding sugar-containing molecules in the column; a denaturing agent; or a chaotrope such as guanidine hydrochloride.

The discovery of the high mannose binding of IL-2-containing hybrid molecules can be taken advantage of, according to the invention, in another way as well, to provide a therapeutic composition composed of such a hybrid compound, e.g., DAB-IL-2, associated in a stable complex with one or more molecules consisting of or containing a hybrid compound-binding complex sugar moiety as defined above. In particular embodiments of the therapeutic composition, the complex sugar moiety consists of ovalbumin, uromodulin, the sugar portion of ovalbumin, a region of the sugar portion of ovalbumin with affinity for the hybrid molecule, the sugar portion of uromodulin, or a region of the sugar portion of uromodulin with affinity for the hybrid molecule. The therapeutic composition can be used in a method of treatment of a patient in need of an IL-2 containing hybrid molecule, e.g., DAB IL-2. The complexation of the IL-2-containing hybrid molecule with the sugar moiety can prolong in vivo half-life of the hybrid molecule, both by adding to its bulk and by slowing the rate of removal of the hybrid molecule from the bloodstream by organs or leukocytes which recognize the sugar moiety less well than they do the uncomplexed hybrid molecule. The complexation of the IL-2 containing hybrid molecule with the sugar moiety can also decrease the toxicity of the hybrid molecule by preventing its entry into cells that do not contain the receptor for IL-2 but do contain surface carbohydrate structures similar to M5[6](e.g. kidney tubule cells, liver hepatocytes, etc.) which may allow transmit into these cells, resulting in their death.

The invention also provides a method of detecting, in a liquid sample, a hybrid IL-2-containing compound as defined above, involving contacting the sample with sugar moiety-containing molecules as defined above, attached to a solid phase to bind the hybrid molecules thereto; contacting labeled anti hybrid antibody with the bound hybrid compound; washing unbound labeled antibody from the solid phase; and detecting the label as a measure of hybrid compound in the sample.

Other features and advantages of the invention will be apparent from the following description of the preferred embodiments thereof, and from the claims.

DESCRIPTION OF THE PREFERRED EMBODIMENTS

The drawings are first described.

Drawings

Methodology

Materials

Figure 1:
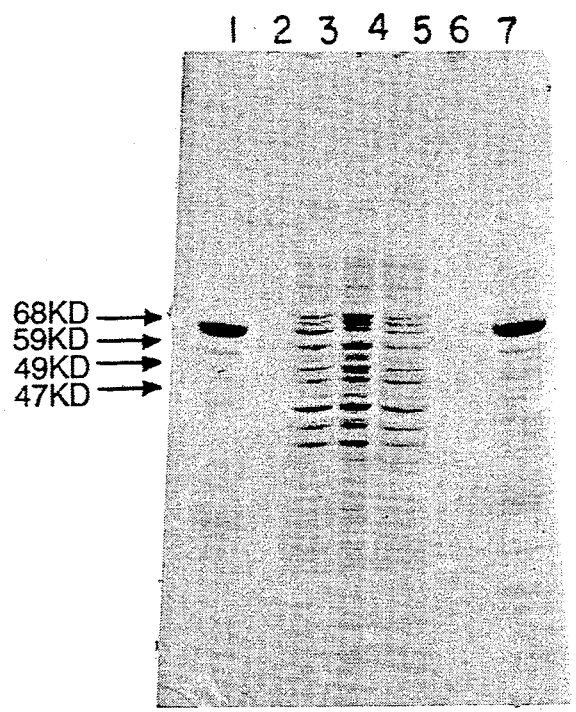
FIG. 1 is an SDS PAGE gel of the protein eluted by 4m guanidine hydrochloride from a column of ovalbumin sepharose which had been incubated with an *E. coli* whole cell lysate containing DAB-IL-2.

Ovalbumin (Lot #38F 82056) and CNBr activated sepharose (Lot #73F-96301) were purchased from Sigma (St. Louis, Mo.). Guanidine hydrochloride (Lot #73F 96301) was purchased from Fluka. Horse anti diphtheria toxin antibody was purchased from Connaught Laboratories (Swiftwater, PA). Anti IL-2 monoclonal antibody 5B3 was made at Seragen, Inc. (Hopkinton, MA). Isopropylthiogalacto pyrannoside (IPTG) was purchased from U.S. Biochemical Corporation (Cleveland, Ohio).

Preparation of Ovalbumin Sepharose

Ovalbumin was covalently linked to CNBr-activated Sepharose 4B according to the manufacturer's (Pharmacia via Sigma) instructions. The initial concentration of ovalbumin in the coupling solution was 5 mg/ml. The coupling efficiency was 60% so that the final concentration of ovalbumin was 3 mg per ml of resin.

Preparation of E. coli Whole Cell Lysate containing DAB-IL-2

Fermentation of *E. coli* transformed with DAB-IL-2 encoding DNA was carried out in a series of five 10L New Brunswick fermenters. At the appropriate cell density, the cultures were induced with IPTG and expression of DAB-IL-2 protein was allowed to proceed over a 60–90 minute period.

After the cultures were induced and had reached the appropriate density, fermenters were harvested. Subsequently, the cells were simultaneously washed, chilled, and concentrated using an Amicon Ultrafiltration system. The cell slurry was centrifuged at 10,000×g for 30 minutes and the pelleted cells resuspended in a lysis buffer consisting of 50 mM potassium phosphate (pH8), 10 mM EDTA, 750 mM NaCL, and 0.1% Tween-20.

Disruption of the cells was accomplished using a Gaulin homogenizer. Cell debris was removed by centrifugation at 10,000×g for 30 minutes. The clarified whole cell lysate was then filtered through 0.22 micron Millipore filters to remove any intact recombinant organisms. The resulting filtered whole cell lysate is a crude mixture of soluble bacterial proteins and recombinant DAB IL-2 product.

Purification of DAB IL-2 on Ovalbumin Sepharose 10 ml of the above *E. coli* whole cell lysate containing DAB-IL-2 was incubated in batch mode with 8 ml of ovalbumin-Sepharose for 15 hours at 4° C. Subsequent to this adsorption step, the resin, along with the whole cell lysate solution, was poured into a Pharmacia K 15 chromatography column. The resin was then washed with high and low salt buffers until the absorbance at 280 nanometers ($A_{280}$) of the column effluent reached a stable baseline. A solution containing the strong denaturant 4M guanidine hydrochloride (GuHCl) was then passed through the column, resulting in the elution of a discrete peak of $A_{280}$ absorbing material. The protein eluted by the GuHCl solution contained 8.0% of the total protein measured in the load fraction, as set forth in Table 1 below.

TABLE 1

| Purification of DAB-IL-2 on Ovalbumin-Sepharose | | | | |
|---|---|---|---|---|
| Fraction | Vol (mls) | Conc (ug/ml) | Total Protein | % Recovery |
| WCL Load | 10 | 5510 | 55.1 | 100 |
| Flowthrough | 20 | 1863 | 37.3 | 68 |
| Wash 1[b] | 40 | 349 | 14.0 | 25 |
| Wash 2[c] | 47 | 50 | 2.4 | 4 |
| 4M GuHCl Elution[d] | 16 | 257 | 4.1 | 8 |
| Re-Equilibration | 49 | 50 | 2.5 | .5 |

Experimental Data

The protein eluted by GuHCl was analyzed by SDS PAGE and Western blotting to determine that it was DAB IL-2. Referring to FIG. 1, SDS-PAGE was carried out to compare a standard consisting of DAB-IL-2, a sample of *E. coli* whole cell lysate, a sample of the fraction flowing through with the first wash, a sample flowing through with the second wash, and a sample of the GuHCl elution fraction. Still referring to FIG. 1, Coomassie-blue-stained SDS-PAGE showed a prominant band at 68kD (Lane 7) that co-migrated with the 68kD product band from a control preparation (Lane 1). Other bands observed on the gel co migrated with known subfragments of DAB-IL-2, e.g., 59kD, 49kD, 47kD, and others. In addition, faintly staining bands co-migrating with ovalbumin were observed. This is to be expected since it is well known that proteins covalently linked to CNBr Sepharose leach from this resin when subjected to strong denaturants such as GuHCl.

Figure 2:
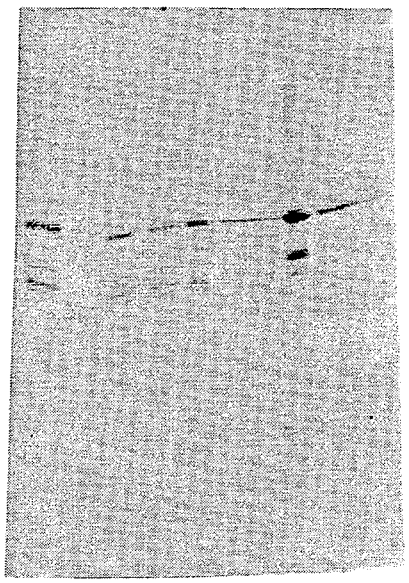
FIG. 2 is a Western blot which was obtained by using horse anti-DT polyclonal antigera.
Figure 3:
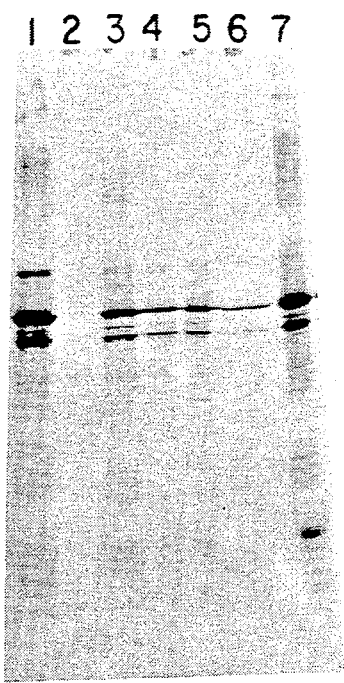
FIG. 3 is a Western blot which was obtained by using 5B3.
Figure 4:
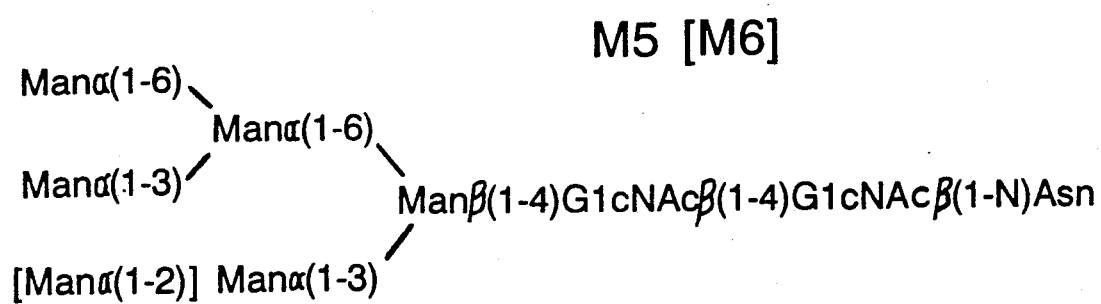
FIG. 4 is a diagrammatic illustration of two forms of the IL-2 binding high mannose sequence M5[6], taken from Sherblom et al., id.

The identity of the DAB IL-2 band (and known subfragments) was confirmed by Western blot analysis using two different antibody preparations known to react specifically with DAB IL-2. The first antibody used in Western blotting was a horse anti DT polyclonal antisera which recognizes diphtheria toxin and DAB IL-2. Referring to FIG. 2, a Western blot analysis using anti-DT polyclonal antisera was performed utilizing samples corresponding to those used in the SDS-PAGE. Still referring to FIG. 2, the results indicated that nearly all of the protein eluted by GuHCl from the ovalbumin Sepharose column was DAB IL-2. The second antibody used in an analogous Western blot analysis was 5B3, a monoclonal antibody that recognizes a specific epitope on IL-2 and the same epitope on DAB-IL-2. Referring to FIG. 3, the Western blot analysis performed with 5B3 also indicated that the protein eluted by GuHCl from the ovalbumin Sepharose column was DAB IL-2.

The foregoing data indicates that DAB IL-2 is capable of binding specifically to the M5[6]high mannose branched chain carbohydrate of ovalbumin.

Other Embodiments

Other embodiments are within the following claims. For example, the purification method of the invention can be used to purify any IL-2-containing hybrid molecules, e.g., molecules in which the IL-2 portion is attached to one or more additional molecules by covalent non peptide bonds (e.g., disulfide bonds); molecules in which the cell physiology-affecting portion, rather than being derived from diphtheria toxin, is another toxin such as Pseudomonas exotoxin or ricin, or a non toxin molecule which affects cell physiology; and molecules containing more than one active component; in addition to IL-2.

What is claimed is:

1. A method for purifying, from a mixture, a hydbrid compound which comprises a portion of IL-2 covalently attached to a cell physiology affecting molecule, said portion of IL-2 comprising at least a region of the IL-2R binding domain of IL-2 effective to cause said hybrid compound to bind to cells bearing an IL-2R, said method comprising:

passing said mixture containing said hybrid compound over a column having attached thereto molecules comprising an M5 or M6 high mannose carbohydrate with affinity for the hybrid compound to bind said hybrid compound to said molecules while permitting the remainder of said mixture to pass through said column without binding to said molecules; and then eluting said hybrid compound from said column.

2. The method of claim 1 wherein said hybrid compound is a hybrid protein comprising a first part, a second part, a third part, and a fourth part
   (a) said first part comprising the enzymatically active Fragment A of diphtheria toxin,
   (b) said second part comprising the cleavage domain adjacent to said Fragment A of diphtheria toxin,
   (c) said third part comprising at least a portion of the hydrophobic domain of Fragment B of diphtheria toxin and not including the generalized eukaryotic binding site of said Fragment b, and
   (d) said fourth part comprising a portion of IL-2, said portion including a region of the IL-2R binding domain of IL-2, said region being effective to cause said hybrid protein to bind selectively to a predetermined class of cells which bear IL-2R and which cells are to be killed by said enzymatically active Fragment A.

3. The method of claim 1 wherein said molecules attached to said column comprise ovalbumin.

4. The method of claim 1 wherein said molecules attached to said column comprise uromodulin.

5. The method of claim 1 wherein said molecules attached to said column comprise the sugar portion of ovalbumin or a region of the sugar portion of ovalbumin.

6. The method of claim 1 wherein said molecules attached to said column comprise the sugar portion of uromodulin or a region of the sugar portion of uromodulin.

7. The method of claim 1 in which said eluant contains a sugar which competes with said molecules in said column for the hybrid compound.

8. The method of claim 1 in which said eluant comprises a denaturing agent.

9. The method of claim 1 in which said eluant comprises a chaotropic agent such as guanidine.

* * * * *